United States Patent [19]

Engelbrecht

[11] Patent Number: 4,872,936
[45] Date of Patent: Oct. 10, 1989

[54] POLYMERIZABLE CEMENT MIXTURES

[75] Inventor: Jürgen Engelbrecht, Hamburg, Fed. Rep. of Germany

[73] Assignee: Ernst Muhlbauer KG, Hamburg, Fed. Rep. of Germany

[21] Appl. No.: 191,650

[22] Filed: May 9, 1988

Related U.S. Application Data

[63] Continuation of Ser. No. 916,589, Oct. 8, 1986, abandoned.

[30] Foreign Application Priority Data

Oct. 9, 1985 [DE] Fed. Rep. of Germany ....... 3536076

[51] Int. Cl.$^4$ ................................................ C09J 5/02
[52] U.S. Cl. ................................ 156/307.3; 156/327;
260/998.11; 433/228.1; 523/116; 523/118;
526/191; 526/194; 526/195
[58] Field of Search ........................... 156/307.3, 327;
433/228.1; 523/116, 118; 526/191, 195, 194;
260/998.11

[56] References Cited

U.S. PATENT DOCUMENTS

| | | | |
|---|---|---|---|
| 3,959,212 | 5/1976 | Rockett et al. | 433/228.1 |
| 4,411,625 | 10/1983 | Koblitz et al. | 433/228.1 |
| 4,591,384 | 5/1986 | Akahane et al. | 433/228.1 |

FOREIGN PATENT DOCUMENTS

| | | | |
|---|---|---|---|
| 0225706 | 6/1987 | European Pat. Off. | |
| 57-75907 | 5/1982 | Japan | 523/118 |
| 1504520 | 3/1978 | United Kingdom | 523/118 |

*Primary Examiner*—John J. Gallagher
*Attorney, Agent, or Firm*—Sprung, Horn, Kramer & Woods

[57] ABSTRACT

The invention concerns polymerizable cement mixtures containing
(a) polymerizable unsaturated monomers and/or oligomers and/or prepolymers containing acid groups and/or their reactive acid-derivative groups,
(b) reactive fillers that can react with these acids or acid derivatives, and
(c) curing agents
that can be employed especially in dentistry as improved dental mixtures as well as in medicine.

36 Claims, No Drawings

POLYMERIZABLE CEMENT MIXTURES

This is a continuation of application Ser. No. 916,589, filed Oct. 8, 1986 now abandoned.

The invention concerns polymerizable cement mixtures, especially those intended for dentistry and medicine.

A number of cements are employed in dentistry for various purposes, especially for instance for securing crowns and inlays as well as orthodontic devices, as root-canal filling material, as underfilling material when introducing dental-restoration material to protect the tooth pulp, and even as the filling material itself. Some of these cements are employed in medicine as bone cements.

Cements for dental and medicinal purposes consist as a rule of a mixture of finely divided metal oxides, metal hydroxides, silicate-cement glazes, or ion-leaching glasses, that is induced to react with a liquid medium that essentially contains phosphoric acid, polycarboxylic acid, or even salicylic-acid derivatives.

Although cements based on phosphoric acid and silicate-cement glazes (silicate cements) or on metal oxides (phosphate cements) exhibit more (silicate cement) or less (phosphate cement) mechanical strength, they are very incompatible with the pulp, too brittle, and too water-soluble.

Cements based on polycarboxylic acids and metal oxides (carboxylate cements) or on ion-leaching glasses (ionomer cements), however, although they are also only more (ionomer cements) or less (carboxylate cements) mechanically strong, are highly compatible with the tissues and exhibit satisfactory adhesion to the dental tissue. Still, they also are too brittle, also have the drawback of washing out too readily in an aqueous environment, and exhibit no chemical bond to acrylic-based filling materials, as well as not adhering to them.

Cements based on salicylates and metal oxides or hydroxides, especially calcium hydroxide, are employed as pulp-capping materials and root-canal filling materials (U.S. Pat. No. 3,047,408). Cements of this type act, due to their high pH, as protective blocks against the acids and other toxic substances that can be included in some filling materials. They also occasion the formation of secondary dentin. The mechanical strength of the cured products, however, is not especially high, and its relatively high water-solubility makes the material dissolve more or less rapidly.

Essential for cements is that they cure by means of ionic reactions like neutralization, salt formation, chelation, or crystallization, specifically in the presence of water.

Different types of cement have turned out to be more or less practical for different applications in dentistry and medicine.

Cements are employed mainly as underfilling materials, as fastening materials, and in exceptional cases, also as filling materials for lesions in the gingival region.

The serious drawbacks of cements, their tendency to wash away and their low mechanical strength, have led to their being extensively replaced as filling materials by the longer-lasting, more stress-resistant, more edge-stable, insoluble, and cosmetically more satisfactory polymerizable acrylic-based filling materials called composites.

Composites consist essentially of a polymerizable binder reinforced with organic or inorganic fillers. Appropriate polymerizable binders are compounds with olefinically unsaturated groups, especially, for dental and medicinal purposes, the esters of the (meth)acrylic acids of univalent and multivalent alcohols, mixed if necessary with other vinyl monomers.

Employed as inorganic fillers are fine quartz powders, microfine silicic acid, aluminum oxide, barium glasses, and other particulate minerals that do not in themselves enter into chemical bonds with the polymerizable binders that surround them and are accordingly usually combined with a coupling agent in the form of a polymerizable silane to ensure satisfactory bonding to the binder. Essential to composites is that they cure via polymerization of the olefinically unsaturated groups in the binder, specifically by means of a radical reaction that does not require the presence of water.

Although composites are what are mainly employed today (in addition to amalgams) as dental restoration materials, there are certain limits to their use. Composites have restricted applications, due to irritation of the tissues or for reasons of toxicity, in relation to deep cavities in the teeth and to restorations of the gingival border and dentin. Furthermore, they do not address to the dental tissue. Such cases usually required cements based on polycarboxylic acids and metal oxides (carboxylate cements) or on ion-leaching glasses (ionomer cements). Restoration materials of this type are less toxic and adhere well to the dental and osseous tissues.

There has been no lack of attempts to improve not only the mechanical strength but also in particular the solubility behavior, miscibility behavior, and compatibility of cements to composites.

To decrease water-solubility for example, polymers such as polystyrenes, polyvinyl acetates, and polyvinyl butyrals or even paraffin oil, linseed oil, colophony, and other natural resins have been added to calcium-hydroxide cements and carboxylate cements. Separation phenomena have been controlled by means of surface-active substances such as zinc stearate or ethyltoluene sulfonamide.

Additives that contain olefinic double bonds, such as esters of 5-methoxyconiferin—called syringates—have, in combination with the addition of radically reacting catalyst, provided cements with better mechanical strength, somewhat lower solubility, and a certain amount of bonding capacity to composites.

The object of the invention is to provide new dental mixtures that not only exhibit essentially the advantages characteristic of cements based on polycarboxylic acid or salicylate, like good adhesion to the dental and osseous tissues, but also demonstrable those of composites, like lower solubility and increased mechanical strength, that can be copolymerized with composites, and that will have no outstanding separation phenomena.

This object is attained in accordance with the invention by means of polymerizable cement mixtures that contain (a) polymerizable unsaturated monomers and/or oligomers and/or prepolymers containing acid groups and/or their salts and/or their reactive acid-derivative groups, (b) reactive fillers that can react with these acids or acid derivatives, and (c) curing agents.

It turns out, surprisingly, that combining some of the polymerizable resin mixtures that have been developed for adhesion to the dental tissue with reactive fillers of this type, which are conventionally contained in cement for setting important constituents, will lead to mixtures that cure both radically and via ionic reactions. The result is a wide range of new composite cements with better properties and new application potentials.

Examples of polymerizable unsaturated monomers with acid groups or reactive acid-derivative groups that are known as good bonding agents for oxidic materials and the dental tissue are unsaturated organic esters of phosphoric and phosphonic acids (German AS No. 2 711 234 & German OS No. 3 150 285), unsaturated organic esters of monofluorophosphoric acid (U.S. Pat. No. 3,997,504), unsaturated organic esters of phosphoric acids that contain either chlorine or bromine bonded directly to the phosphorus (Eur. Pat. No. 0 058 483), unsaturated organic esters of phosphoric acid in the form of pyrophosphates (anhydrides) (German OS No. 3 048 410), and 4-methacryloyloxyethyltrimellitic acid and its anhydride (M. Takeyama et al., I. Jap. Soc. f. Dent. App. a. Mat. 19, 170 [1978]), and bis-2-methacryloylethyl pyromellitate.

Examples of powdered constituents commonly contained in cements because important for setting are specified for instance in German Patent No. 2 061 513, Swiss Patent No. 588 863, German OS No. 2 751 069, German OS No. 2 750 326, U.S. Pat. No. 4,250,277, European Patent No. 0 023 013, and U.S. Pat. No. 4,376,835.

The polymerizable unsaturated monomers, oligomers, or prepolymers in the polymerizable cement mixtures in accordance with the invention can carry alkenyl, alkenoxy, cycloalkenyl, aralkenyl, or alkenaryl radicals, with acryl, methacryl, vinyl, or styryl radicals being practical and, of these, the acryl and methacryl radicals, which constitute the polymerizable groups in many monomers, being especially practical.

Especially appropriate acid groups are all those that can react with oxidic, mineral, ceramic, vitreous, or metallic fillers. It is practical however for these acid groups to be carboxylic-acid radicals, the radicals

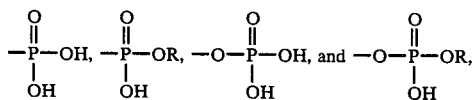

of phosphorus acids wherein R is alkyl, aryl, or vinyl for example, the radicals —SO$_2$H, SO$_3$H, or —O—SO$_3$H of sulfuric acids, and the radicals

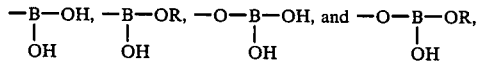

of boron acids wherein R is alkyl, aryl, or vinyl.

Cationic acid radicals like —NR$_2$H$^+$ or —PR$_2$H$^+$ (wherein R is H or alkyl) are also appropriate.

The reactive acid derivatives can be substituted with acid halides, with acid anhydrides, and with acid amides, nitriles, and esters, that readily hydrolyze into acid, such can enter into ion-exchange, neutralization, salt formation, or chelation reactions with the reactive filler.

Especially preferred are acid groups or reactive acid derivatives in the form of carboxylate, phosphate, phosphonate, sulfonate, or borate acid radicals or of their reactive derivatives.

Especially appropriate are compounds that contain at least two polymerizable groups or at least two acid groups or acid-derivative groups. Examples are phosphoric-acid esters of glycerine dimethacrylate or 1-methacryloxyethane-1,1-diphosphonic acid.

Very especially preferred are compounds that contain at least two polymerizable groups and at least two acid groups, such as the chloro- or bromophosphoric-acid esters of bisphenol-A-glycidyl dimethacrylate (bis-GMA), which can easily be prepared by reacting bis-GMA with phosphoryl chloride and whereby the ratio of phosphorus to bis-GMA is 2:1.

Examples of polymerizable unsaturated oligomers or prepolymers with acid groups or acid-derivative groups are compounds that contain not only polymerizable groups but also acid groups or acid-derivative groups bonded to chemically highly stable molecular backbones.

It is practical for the polymerizable unsaturated oligomers or prepolymers to contain two unsaturated groups and/or two acid groups or two reactive acid-derivative groups and especially practical for them to contain three or more unsaturated groups and three or more acid groups or three or more reactive acid-derivative groups.

Compounds of this type are very satisfactory as constituents of agents for bonding to an oiidic, mineral, ceramic, vitreous, metallic, or biological substrate, especially the dental tissue, and are especially appropriate as constituents of the cement mixtures in accordance with the invention.

The molecular backbones of compounds of this type can be linear, branched, or cyclic.

They can be polymers of ethylenically unsaturated monomers or they can be oligomeric or polymeric compounds, such as polyesters, polyamides, polyethers, polyphosphazenes, polysaccharides, etc. for instance, if their backbone is sufficiently hydrolysis-stable, if they can be supplied with the desired polymerizable groups, and if they include or can be supplied with the desired acid groups.

The desired groups can be grafted if the backbone contains a number of bound functional groups, such as alcohol, halogen, acid halide, amino, epoxide, or isocyanate groups, that allow such a grafting reaction.

This means that the aforesaid backbones can, no matter what components they are constructed of, usually polyalcohols, polyhalides, polyacid halides, polyamines, polyepoxides, polyisocyanates, or polyanhydrides, lead either alone or in mixtures to the oligomeric or polymeric compounds in the mixtures in accordance with the invention. Preferred backbones are polymers of ethylenically unsaturated monomers.

The preferred oligomeric or prepolymeric backbone compounds that are preliminaries in the preparation of the preferred oligomeric or prepolymeric compounds can be prepared from polymerizable monomers by appropriate reactions that convert them into oligomers or polymers of various degrees of polymerization.

A group of monomers that results in homo-oligomers or homopolymers is appropriate on the one hand, and, on the other, a group that results in co-oligomers or co-polymers by means of a combination of different monomers. Oligomers or polymers of unsaturated acids employed in the acid-chloride form,

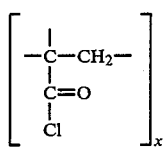
(A)

are appropriate examples from the homopolymer group. They can be converted to a desired level with hydroxyethyl method is desired, with the acid-chloride radical being hydrolyzed in a second step. The statistical distribution of the grouped is for example

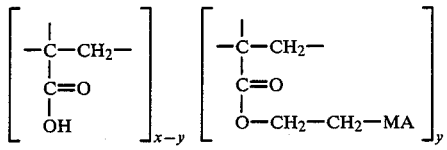
(B)

wherein MA is a methacryloyloxy radical

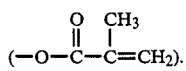

The second stage (hydrolysis) can, however, be replaced by means of alcoholysis with alcohols, such as a 1-hydroxy-ethane-1,1-diphosphonic acid, that contain acid groups to obtain products such as

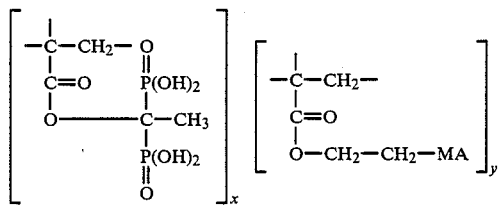
(C)

Another good backbone for compounds in accordance with the invention is provided by homopolymers of unsaturated alcohols (D). Some of the hydroxy groups can be provided with polymerizable groups by for example esterification with an unsaturated acid or with an unsaturated acid chloride. Others can be converted into corresponding compounds (E) and (F) in accordance with the invention, by means of acids or acid chlorides such as boric acid or phosphoryl chloride for example.

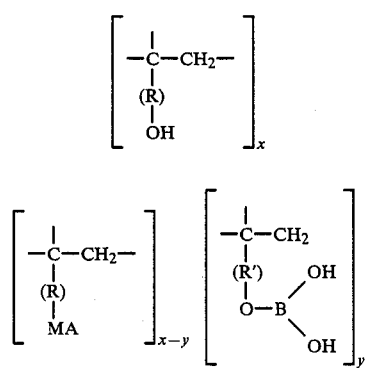
(B)

(E)

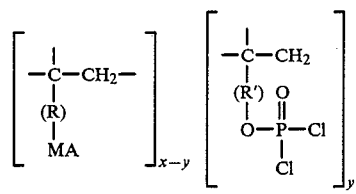
(F)

wherein R and $R^1$ are absent or are inert radicals.

Especially preferred are oligomers or polymers of maleic acid anhydride:

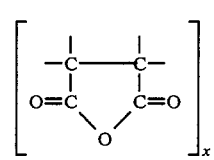

which can be converted with a hydroxyalkyl methacrylate for instance in a ratio of 1:1 into products such as

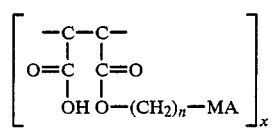
(G)

A product with two different adhesive groups in accordance with the invention,

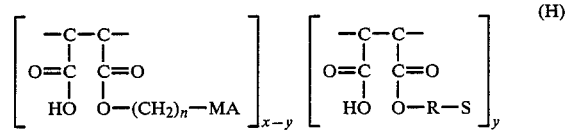
(H)

wherein S is absolutely any acid radical or acid-derivative radical and R is any radical, can be obtained by adding less hydroxymethacrylate and making up for it with more of the hydroxy-acid derivative.

In another group of preferred fundamental compounds-specifically co-oligomers or co-polymers—vinyl, styrene, or (meth)acryl monomers such as vinyl phosphate, vinyl phosphonate, methacrylates of phosphoric acids or phosphonic acids, and styryl compounds with phosphoric, boric, and sulfuric acid groups, such as sulfonated styrene for example, that contain acid or an acid derivative can be copolymerized with unsaturated compounds such as vinyl chloroacetate or chloromethylated styrene into compounds such as for example

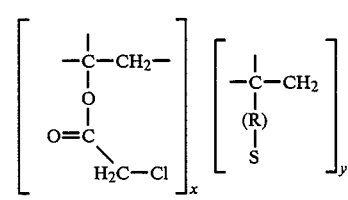
(I)

or, for example

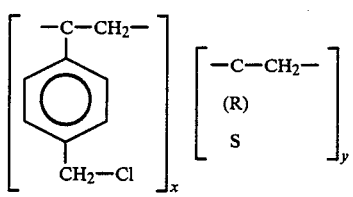 (K)

Compounds of this type can then be converted with sodium methacrylate for example into a polymerizable compound

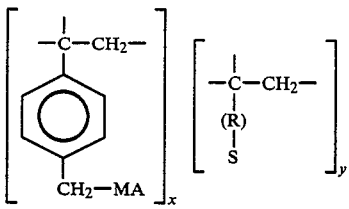 (L)

in accordance with the invention.
Copolymers

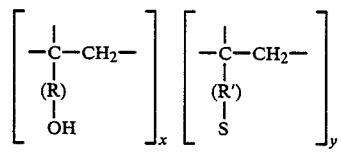 (M)

of unsaturated alcohols and unsaturated acids also result subsequent to reaction with compounds such as methacrylic-acid chloride also result in products

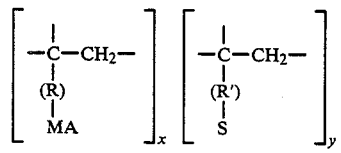 (N)

in accordance with the invention.

In constructing the backbone, units that do not have acid groups and that are not supplied with a polymerizable group can also be polymerized in. It can on the one hand be practical to do so in order to modify the solubility, as for example by inserting inert methyl-methacrylate units

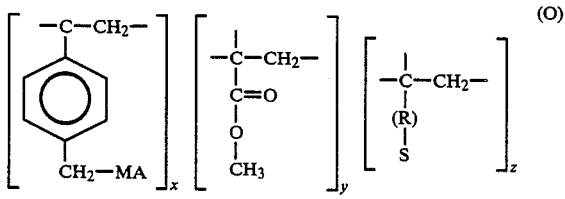 (O)

The insertion of additional units with halotriazine, epoxide, isocyanate, or aldehyde groups

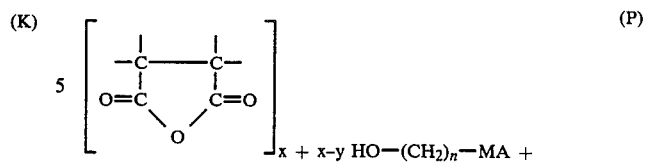 (P)

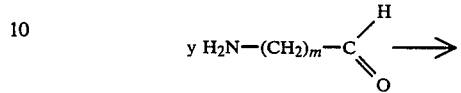

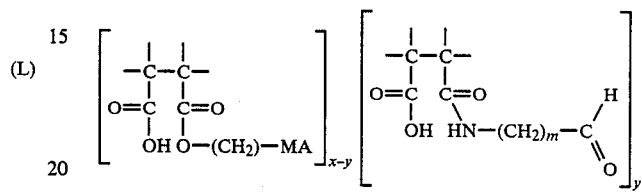

can on the other hand also be useful to induce an additional reaction with the collagen constituent of the dental or osseous tissue. The aldehyde groups may also be in the form of acetals or semi-acetals The insertion of units with groups that can be components of a polymerization-catalyst system can be of advantage. The groups do not absolutely have to be present as groups of that kind during the homo- or co-polymerization of the backbone, but can be grafted on subsequently by means for example of a halogen-, alcohol-, anhydride-, or amine-functional group.

The reaction methods that result in the oligomeric or prepolymeric fundamental compounds can be determined by the choice of solvent, solubilities, concentration, temperatures, and polymerization catalysts and are known to one skilled in the art.

It can be important for the polymerization catalysts to be destroyed by the reaction itself or for any residues to be removed before the polymerizable groups in accordance with the invention are introduced.

It is practical for the oligomeric compounds to have a molecular weight of more than 500, and for the prepolymeric compounds to have one of greater than 1500, although preferably no greater than 100,000, and particularly preferably no greater than 20,000.

The mixtures in accordance with the invention can also contain other polymerizable unsaturated monomers and/or oligomers and/or prepolymers that do not contain any acid groups and/or salts thereof and/or reactive readily hydrolyzing acid-derivative groups thereof. Particularly appropriate are monomers that are constituents of conventional composites such as for example bis-GMA or triethyleneglycol dimethacrylate. The mixtures can also if necessary contain other compounds that, although they contain acid groups and/or their salts and/or their reactive readily hydrolyzing derivative groups do not contain any groups that are unsaturated and polymerizable. Preferred in this case are multi-basic acids or their reactive, readily hydrolyzing derivatives. Especially preferred multibasic acids are hydroxy acids such as tartaric or citric acid, but also polyacids such as polycarboxylic, polyphosphoric, polyphosphonic, or polysulfonic acids.

Compounds that have chelating groups but do not contain acid groups or readily hydrolyzing acid-derivative groups can be employed. Examples of this type are vanillates, syringates, and salicylates.

The proportion of polymerizable compounds that contain acid groups or reactive acid-derivative groups in the overall content of the polymerizable compounds in especially preferred mixtures ranges from 20 to 60% and in preferred mixtures from 5 to 100%, although mixtures with less than 5% also definitely exhibit the features peculiar to those in accordance with the invention. It can simultaneously be practical for example to allow the portion or some of the portion of the polymerizable compounds that contains the acid groups or acid-derivative groups to absorb onto the filler before the reactive fillers are worked in and sometimes to let it react (ionically) with the surface via traces of water, before, however, the polymerizable double bonds can react. The latter must not occur until the preliminarily treated fillers are mixed into the overal mix and while they themselves are polymerizing.

Appropriate reactive fillers for the composite-cement mixtures in accordance with the invention that react with acid groups or acid-derivative groups in the polymerizable compounds are mainly metal compounds, glasses or ceramics that contain metal compounds, zeolites, oxidizable metals, and boron nitride, as well as the products derived from sintering these constituents. A prerequisite is that the fillers are present in a finely divided form, that they can react ionically with the acid groups in the polymerizable monomers accompanied by a certain amount of hardening or curing, and the reaction products are as insoluble as possible. It can be sufficient and may even by desirable for this reaction to occur only on the surface of the filler.

Thus, sintering products of powders of the aforesaid metal compounds, glasses, ceramics, zeolites, or non-precious metals can also, in combination with powders of precious metals, other glasses and ceramics, $SiO_2$, and aluminum oxides etc. that are generally common in composites in the capacity of inorganic fillers but that in themselves do not react or hardly react with polymerizable monomers that contain the acid groups, result in useful fillers.

It can absolutely be sufficient or even practical for the stage or curing that accounts for the actual cement reaction and that occurs via ionic reactions not to occur until the material is in the mouth, as the result of moisture penetrating into the polymerized cement material. Practically appropriate for composite-cement mixtures in accordance with the invention are metal oxides and metal hydroxides, with the metals being calcium, magnesium, or zinc in particular.

Also preferred are powder of silicate cements, powder of ionomer cements (ion-leaching glasses), or powder of ion-exchanging zeolites, whereby the release or exchange of calcium is especially preferred. Even mixing or sintering powder of silicate cement, ionomer cement, or zeolite with powdered silver or silver alloys and grinding the sintering products will lead to preferred embodiments.

The reactive fillers do not absolutely have to be the only fillers in the mixtures in accordance with the invention. Other fillers of the type conventional in composites which are not reactive in the sense of ionic reactions or cement-setting reactions can be mixed in especially when silanized. This can be an advantage for example if the cured products are to exhibit high mechanical or chemical resistance. It can likewise be necessary to divide the mixtures in accordance with the invention into separate constituents for storage purposes, with one constituent containing the polymerizable monomers with the acid groups and the nonreactive filler and the other constituent containing the polymerizable monomers without the acid groups and the reactive filler.

The proportion of reactive to total filler in preferred mixtures is higher than 5% by weight and is higher than 30% by weight in especially preferred mixtures. In some cases, however, even lower portions can have a definite effect, on alkalinity for example, which can be important for filling materials in the field of dentistry. The total filler content in the mixtures in accordance with the invention is in particular between 10 and 95% and preferably between 30 and 85% (by weight) of the total.

Appropriate polymerization catalysts in principle are all those systems that can trigger the radical polymerization of olefinic compounds. Whether the catalyst reaction is initiated by heating, by the introduction of an activator, or by photoirradiation is not essential. What is important, however, is for the catalyst system to dissolve satisfactorily in the mixture and essentially not be blocked or disintegrated by polymerizable compounds that contain acid groups or acid-derivative groups.

Preferred for light-curing (photocuring) mixtures are curing systems consisting of $\alpha$-diketones and tertiary amines such as those specified in French Patent No. 2 156 760 for instance or of combinations of sulfinic-acid salts and of xanthones or thioxanthones such as those specified in European Patent No. 0 132 318 for instance.

Especially appropriate for bicomponent mixtures are combinations of one constituent that contains organic peroxides and of another constituent that contains a tertiary amine and a compound that exhibits sulfur in oxidation number $+2$ or $+4$. The constituent that does not contain the peroxide can preferably also contain bivalent metal ions, especially that of calcium, particularly when tertiary butyl permaleate is employed as the peroxide. Especially preferred are benzoyl peroxide for the organic peroxide and sodium para-toluene sulfinate as the sulfur compound.

An especially practical mixture results when alcohols that contain one or more polymerizable olefinic unsaturated groups are added to the constituent that contains the sodium sulfinate to ensure adequate solubility of that salt.

Appropriate for this purpose are for example hydroxyalkyl methacrylates such as hydroxyethyl methacrylate or vinyl compounds, such as allyl alcohol, that contain hydroxy groups, and especially dimethacrylate compounds, such as bisphenol-A-glycidyl methacrylate or glycerol dimethacrylate, that contain hydroxyl groups, and divinyl compounds, such as glycerinediallyl ether, that contain hydroxyl groups. It is generally necessary to add 10 to 20% of these polymerizable monomers that contain hydroxyl groups.

Curing agents that are typical for cements and that accelerate the ionic reactions, such as water or even tartaric acid or mellitic acid, can also be added.

The composite cements in accordance with the invention can of course also contain conventional plastic additives, like pigments, UV stabilizers, antioxidants, etc., that have in a known way a beneficial effect on the appearance and stability of the still uncured pastes or of the cured products. Slight amounts of salts of heavy metals like iron, copper, manganese, cobalt, tin, chromium, nickel, and zinc can likewise be added to promote adhesion to the dental tissue for example. Curative constituents such as cortisone or corticoids, oleum pedum tauri (neatsfoot oil), etc. can also be added, not for purposes of physical chemistry but if indicated for strictly medicinal purposes. The function of the composite cement will then be not only that of a cement and in certain cases of a donor of calcium ions or contributor to the pH, but also of a pharmaceutical form. Compounds, such as sodium fluorophosphate or aminofluorides, that donate fluoride, can also be added for similar reasons.

The composite cements in accordance with the invention to some extent exhibit the outstanding properties that have previously been ascribed only to composites or only to cements. They are in cost cases distinguished by good breaking strength and edge stability, satisfactory hardness, low brittleness, and good tissue compatibility, and even demonstrate the potential of highly alkaline-reacting plastic fillings. They are contain a comparable filler. Acrylic-based filling materials constructed on polymerizable unsaturated monomers can be copolymerized and provide a secure chemical bond. They also securely adhere chemically via ionic reactions to cements and to the dental tissue.

It is also possible to obtain light-curing (photocuring) composite cements.

Not of the least importance is that it is hardly necessary any longer to add paraffin oil, polymers, linseed oil, surface-active substances, etc. as in some type of cement for reasons of consistency or solubility. The polymerizable compounds that contain acid groups or acid-derivative groups wet the inorganic fillers admirably.

One interesting property of the new composite cements is that, although polymerization shrinkage does occur during setting, the process is nullified or even overcompensated simultaneously or subsequently by water intake (e.g. hydration processes). This process can be controlled by the amount of water present in the unpolymerized mixture as well as by the humidity of the ambient medium subsequent to polymerization.

The composite cements in accordance with the invention are appropriate, depending on composition, for root-canal fillings, pulp capping, underfilling, filled cavity liners, and filling materials, as well as as cements for crowns and inlays and orthodontic adhesives, as protective films for etched enamel, as adhesive opaques, and as adhesion-promoting intermediate layers between cements and composites. Not least important, polymerizable- hard, and very break-resistant dental plaster can be prepared. They also have a potential for employment as bone cements and as cements for general purposes.

The composite cements in accordance with the invention are also appropriate for producing casts, in which case they can be employed directly and in conjunction with metal armatures. They are particularly appropriate as implants, especially when the casts include calcium compounds.

The preparations that will now be specified are intended to illustrate the invention. Proportions are in terms of percent by weight unless otherwise specified.

PREPARATION 1. A POLYMETHACRYLATED OLIGOMALEIC ACID 260 g of maleic-acid anhydride were refluxed with 2000 ml of toluene and 40 g of benzoyl peroxide for 6 days. A brownish-orange precipitate occurred. Upon termination of the residue washed with hexane. The yield was 200 g, which was treated with an equal volume of tetrahydrofuran.

A mean molecular weight of 439 was determined, corresponding to an approximate oligomerization degree of 4 maleic-acid anhydride units. The IR spectrum exhibited the C=O band of anhydride groups (1790 cm$^{-1}$) but no acid-OH or double bonds. 100 g of the solution of oligomaleic-acid anhydride in tetrahydrofuran were treated with 10 g of powdered zinc, stirred, and filtered again. The solution was definitely light in color.

60 g of hydroxyethyl methacrylate and catalytic volumes of orthophosphoric acid were added and the batch was allowed to stand for 2 weeks. The mixture was definitely viscous. Drawing off the volatile constituents in the vacuum and washing the batch in hexane resulted in a viscous oil that dissolved very well in acetone and in TEDMA and bis-GMA as well.

The anhydride C=O band in the IR spectrum was almost invisible, although an acid-OH band and a double-bond band were definitely evident.

PREPARATION. 2. A POLYMETHACRYLATED POLYCARBOXYLPOLYPHOSPHONIC ACID

Powdered zinc was stirred into 100 g of the solution of oligomaleic-acid anhydride in tetrahydrofuran from Preparation 1, and the batch was treated with 30 g of hydroxyethyl methacrylate.

The mixture was allowed to react for 2 weeks at room temperature. 40 g of hydroxyethane-1,1-diphosphonic acid was dissolved therein and the batch was allowed to stand for 2 more weeks.

Extracting the tetrahydrofuran resulted in a rather viscous liquid, which was washed with hexane. The IR spectrum exhibited C=C bands at 1640 cm$^{-1}$ and P(O-)OH bands at 1200 cm$^{-1}$. The substance reacts like an acid and turns yellow when activator and peroxide are added.

PREPARATION 3. A PREPOLYMERIC POLYMETHACRYLATED POLYMALEIC ACID 60 g of maleic-acid anhydride and 9 g of lauroyl peroxide were refluxed for 4 days in 150 ml of tetrahydrofuran. The tetrahydrofuran was extracted and the resulting viscous oil washed with hexane.

The polymaleic-acid anhydride has a molecular weight of 1850, corresponding to approximately 17 units. The IR spectrum was identical with that of the oligomaleic-acid anhydride from Example 4.

9.8 g of the oil were dissolved in 30 ml of THF and stirred with 2 g of hydroxy ethyl methacrylate for two weeks. The THF was extracted, leaving a viscous oil of polymethacrylated polymaleic acid with an IR spectrum identical to that of the polymethacrylated oligomaleic acid from Preparation 1.

PREPARATION 4. PREPOLYMERIC POLYMETHACRYLATED POLYCHLOROPHOSPHORIC ACID 42 g of hydroxyethyl methacrylate and 8 g of lauroyl peroxide were dissolved in 400 ml of toluene and allowed to stand for 1 hour at 65° C. The resulting powder was filtered out, washed with hexane, and dried.

The yield was 40 g of polyhydroxyethyl methacrylate (polyHEMA). The molecular weight was 5700, approximately 44 monomer units. The IR spectrum was identical to that of the high-molecular poly-HEMA product manufactured by the firm of Aldrich.

8 g of methacrylic-acid chloride and 8 g of triethylamine were stirred into 13 g of the laboratory poly-HEMA over a period of 3 days. The precipitate was washed with water and dried.

The yield was 15 g of partly methacrylated poly-HEMA.

3.3 g of this powder were added along with 1.5 g of phosphoryl chloride to 50 ml of tetrahydrofuran, and the batch was stirred over a period of 4 days at room temperature. The precipitate was filtered out and washed with hexane, resulting in 3.8 g of a white powder. Its IR spectrum can be satisfactorily equated with that of a polymethacrylated product with —O—P—(O)Cl$_2$ groups. The powder hardly continues to exhibit any C—OH bands but still has the C=O (1730 cm$^{-1}$) and C=C (1640 cm$^{-1}$) bands as well as revealing new bands in the P—O—alkyl range (1030 cm$^{-1}$).

PREPARATION 5. A POLYMETHACRYLATED POLYSULFONATE 5.4 g of hydroxyethyl methacrylate, 10.1 g of potassium methacryloylpropylsulfate, and 1.6 g of lauroyl peroxide were heated in 80 ml of methyl alcohol and 20 ml of toluene at 65° C. until termination of precipitation. The batch was filtered and the filtrate washed with hexane and dried.

The yield was 6.4 g of a water-soluble, powdery molecular weight of 7490, corresponding to approximately 20 units for each of the monomers employed.

1.88 g of the copolymer was stirred along with 0.54 g of methacrylic-acid chloride and 0.50 g of triethylamine in 50 ml of tetrahydrofuran for 4 days at room temperature. The precipitate was washed with hexane and dried.

The yield was 1.92 g of a white, water-soluble, powdery polymethacrylic polypotassium sulfonate, continuing to exhibit a C=C band at 1640 cm$^{-1}$. The potassium content was 7.9% and the sulfur content 6.2%.

PREPARATION 6. A POLYMETHACRYLATED POLIBORIC ACID 3.3 g of the partly methacrylated poly-HEMA from Preparation 4 were heated with 3.1 g of boric acid and 4.1 g of phosphoric acid in dioxan at 80° C. until termination of precipitation.

The batch was filtered, the filtrate washed free of phosphate and boric acid with water, and dried, yielding 3.45 g of a tannish polymethacrylated poliboric acid.

The C=C and C=O bands in the IR spectrum are unchanged and new (B—OH) bands appear at 3220 cm$^{-1}$. The boron content turns out to be 2.4% by weight.

EXAMPLE 1. PREPARATION OF A BICOMPONENT COMPOSITE CEMENT BASED ON HALOPHOSPHORYLATED BIS-GMA AND POWDER OF PHOSPHATE CEMENT (ZnO/MgO)

Different bicomponent mixtures were prepared and reacted.

First component

A resin mixture was prepared from
10 parts bisphenol-A-glycidyl methacrylate (bis-GMA)
10 parts triethyleneglycol dimethacrylate (TEDMA)
1 part phosphoryl chloride.

The mixture was allowed to stand for 5 days at room temperature (Resin 1, the polymerizable halophosphoric-acid compound specified in European Patent No. 0 058 483).

Some of Resin 1 was catalyzed with 1% benzoyl peroxide (Resin 2).

A catalyst paste was prepared by thoroughly mixing 22 parts of Resin 2 and 78 parts of finely ground silanized barium glass (the non-reactive filler). This mixture was thick and pasty.

Second component

A resin mixture (Resin 3) was prepared from
50 parts bis-GMA
50 parts glycerin dimethacrylate (both being polymerizable compounds without acid groups)
1 part N,N-bis-hydroxyethyl para-toluidine
3 parts sodium benzene sulfonate
1 part water
0.002 parts iron oxalate.

An *activator paste* was prepared by mixing 24 parts of Resin 3 and 76 parts of the powder components of Harvard Phosphate Cement (a phosphate cement manufactured on the basis of zinc oxide and magnesium oxide by the firm of Hoffman and Richter, Berlin: the reactive filler).

The catalyst paste was mixed with the activator paste, and the material cured in 1 to 2 minutes. A Barcol hardness of 54 was measured approximately 30 minutes later. The compressive strength was 1800 kg/cm$^2$ subsequent to being kept wet for 24 hours at 37° C. This cement in accordance with the invention proved to be highly tissue-compatible and was satisfactory as a bone cement.

EXAMPLE 2. CONTROL FOR EXAMPLE 1

The powder components of the Harvard cement were cured with the aqueous polyacrylic acid (Voco-Chemie, Cuxhaven, mfr.). Curing occurred within the interval of 5 to 8 minutes conventional for carboxylate cements.

After 30 minutes it was hardly possible to establish a Barcol hardness. The indenter drove into the cast without meeting much resistance and fractured readily. A low level, below 5, was measured subsequent to 3 hours. The material was also very fragile. The compressive strength subsequent to being kept wet for 24 hours at 37° C. was only 550 kg/cm$^2$. This order of magnitude has also been demonstrated for other classic carboxylate cements. Even products improved by the addition of inert fillers such as powdered quartz, polymers, or chelating agents to the cement exhibited compressive strengths of only 800–900 kg/cm$^2$.

EXAMPLE 3. A CURING BICOMPONENT COMPOSITE CEMENT BASED ON HALOPHOSPHORYLATED BIS-GMA AND POWDER OF IONOMER CEMENT

An *activator paste* was prepared by adding 7 parts of Fuji ionomer-cement powder (G-C Dental Corp., Japan, mfr.) to 3 parts of the Resin 3 from Example 1. This paste was mixed with equal amounts of the catalyst paste from Example 1. The material cured rapidly. A Barcol hardness of 57 was measured 30 minutes later. The compressive strength subsequent to being kept wet for 24 hours at 37° C. was 2100 kg/cm$^2$. No dissolution was demonstrable subsequent to being kept in water for 24 hours at 37° C.

EXAMPLE 4. TWO MIX-CURING PASTES BASED ON POLYMETHACRYL-POLYCARBOXYLIC ACID AND POWDER OF PHOSPHATE CEMENT

Two curing pastes were mixed.
The first paste (Resin 4) was prepared from
90 parts triethyleneglycol dimethacrylate
7 parts polymethacrylpolycarboxylic acid (Prep. 1)
2 parts benzoyl peroxide.

This resin was filled to 68% with silanized amorphous sintered silicon dioxide and represented the catalyst paste.
For the second paste a mixture of
50 parts bis-GMA
50 parts hydroxyethyl methacrylate
1 part N,N-bis-hydroxyethyl para-toluidine
3 parts sodium benzene sulfonate were kneaded with phosphate cement. The filler in this *activator paste* accounted for 75%. The activator and catalyst pastes were mixed to initiate curing.

The cured composite cement has a compressive strength of 1500 kg/cm$^2$. The Barcol hardness was 51. The material exhibited no fatigue subsequent to 4000 cycles of stress testing (immersions in water at temperatures alternating between 0° and 60° C.). The Barcol hardness in fact actually increased to 59, and the material was extremely edge-stable. It adhered very well to bovine dentin and enamel.

EXAMPLE 5

A highly alkaline cement mixture was obtained by mixing equal parts of an *activator paste* consisting of
24 parts Resin 3 (Ex. 1)
22 parts calcium hydroxide
22 parts barium sulfate with the *catalyst paste* from Example 1 and allowing it to cure.

The material was hard even a few minutes later, with a Barcol hardness of 20 and a compressive strength of 2000 kg/cm$^2$. The pH was over 11, and the product accordingly highly water-resistant. Given these properties and the fact that Ca(OH)$_2$ preparations stimulate secondary dentin formation, this X-ray opaque cement was extraordinarily effective as an underfilling material, as a root-canal filling material, and as a cement for securing metal pins in restoring stumps. Even improved Ca(OH)$_2$ cements based on polycarboxylic acids or salicylates exhibited maximum compressive strengths of only 300 kg/cm$^2$. Furthermore, they are known to fall apart in a few years, leaving hollow spaces. The latter cannot be expected of the composite cements in accordance with the invention, which are permeated by polymer networks.

EXAMPLE 6

Another polymerizable Ca(OH)$_2$ cement was obtained by mixing
50 parts triethyleneglycol dimethacrylate
50 parts polymethacrylpolycarboxylpolyphosphonic acid
(Prep. 2)
1 part butyl permaleinate and by mixing 6 parts of this mixture with 5 parts of calcium hydroxide and 5 parts of barium sulfate.
The mixture hardened in 5 to 7 minutes.

EXAMPLE 7.

A light-curing Ca(OH)$_2$ cement was obtained by mixing
50 parts triethyleneglycol dimethacrylate
50 parts polymethacryloligomaleic acid (Prep. 1)
1 part camphor quinone
1 part dimethylaminoethyl methacrylate
50 parts calcium hydroxide
50 parts barium sulfate.

The mixture was light-cured in a Litema HL-150 halogen-lamp apparatus for 1 minute. The surface hardened in 40 seconds, and another layer of light-curing Composite Merz could be polymerized onto it immediately.

All of the polymerizable cement mixtures prepared as specified with reference to Examples 1 through 6 can also be copolymerized with polymerizable plastic filling material or resin materials based on unsaturated olefinic compounds. Thus, a secure bond can be obtained between composite cements in accordance with the invention and conventional composites.

EXAMPLE 8. PREPARATION OF A LIGHT-CURING COMPOSITE IONOMER CEMENT.

5 g of a mixture of
50 parts bis-GMA
50 parts triethyleneglycol dimethacrylate
20 parts polymethacryl=ted polymaleic acid (Prep. 3)

are absorbed onto 30 g of the powdered component of the ionomer cement Ceramfil Alpha (PSP Dental, Belvedere, Kent, UK, mfr.) with a solution of ethyl alcohol and dried.

5 g of this powder are thoroughly mixed with 5 g of the polyacrylic-acid coated, powdered ionomer powder from the product Ceramfil Beta, Aqua Set (PSP Dental) to create a new ionomer-cement powder (I) for the light-curing ionomer cement.
A liquid (II) is prepared from
15 g H$_2$O
10 g hydroxyethyl methacrylate
0.15 g N,N-bis-hydroxyethll para-toluidine
0.45 g sodium benzene sulfonate
0.08 g camphor quinone.

The powder (I) is mixed with the liquid (II) to the consistency of a paste (app. 4 parts powder to 1 part liquid). Some (A) of the mixture is kept in the dark and some (B) cured under a Litema HL-150 halogen lamp.

Portion A begins to cure in 10 minutes and is finished in 20 minutes. A 2-mm thick coating of portion A, however, is well cured in 40 seconds.

Samples of Portions A and B are prepared in accordance with DIN Standard 13 922 and their transverse strength measured 3 hours later.

Samples were also prepared by mixing up the glass-and-ionomer cement Ceramfil Beta, Aqua Set (powder and water). Curing commenced in 5 minutes and they were well cured in 10 minutes. Their transverse strength was also measured 3 hours later.

| Transverse strengths | | |
|---|---|---|
| Light-curing ionomer cement (light-cured) | Light-curing ionomer cement (dark-cured) | Ceramfil Beta, Aqua Set ionomer cement |
| 11.6 (3 h) | 6.3 (3 h) | 12.1 (3 h) |
| 43.0 (20 h) | 8.8 (20 h) | 13.2 (20 h) |

EXAMPLE 9. A LIGHT-HARDENING IONOMER CEMENT

A mixture of 1.50 g of polymethacrylated polychlorophosphoric acid (Prep. 4) and 0.25 g of triethylene glycol dimethacrylate in ethyl alcohol is absorbed onto 1.75 g of the ionomer-cement powder from Ceramfil Beta, Aqua Set and dried (powder component).

A reaction partner (liquid component) is prepared from a mixture of
  150 parts hydroxyethyl methacrylate
  50 parts water
  1 part camphor quinone
  2 parts N,N-bis-hydroxyethyl para-toluidine
  5 parts sodium benzene sulfonate.

4 parts of the powder component and 1 part of the liquid component are mixed to the consistency of paste. Some is cured under a halogen lamp (20 sec) and some left in the dark (until it cured, in about 50 min).

3 hours later the sample cured under the halide lamp exhibited a transverse strength of 18.4 N/mm² and, 20 hours later, one of 27.2 N/mm².

EXAMPLE 10. A ROOT-CANAL FILLING MATERIAL

Equal parts of a paste consisting of
  12 parts hydroxyethyl methacrylate
  11 parts glycerin dimethacrylate
  1 part N,N-bis-hydroxyethyl para-toluidine
  76 parts Ceramfil Alpha ionomer powder and of a resin consisting of
  5 parts of polymethacrylated polyboric acid (Prep. 6)
  50 parts bis-GMA
  45 parts triethyleneglycol dimethacrylate
  3 parts benzoyl peroxide were mixed and employed to fill an excavated root canal. The mixture solidifies in 2 minutes. The tooth is left in a methylene-blue bath for 14 days, sliced longitudinally, and polished. No penetration of the dye between the dental tissue and the filler material is demonstrable.

EXAMPLE 11. AN ADHESIVE CEMENT

A fraction with a particle size of less than 20 μm was screened out of the silicate-cement powder from the product Omnifil (Jota, Germany, mfr.). 100 parts were mixed into a paste (I) with
  0.3 parts sodium benzene sulfonate
  0.4 parts N,N-bis-hydroxyethyl para-toluidine
  7 parts bis-GMA
  8 parts triethyleneglycol dimethacrylate.

5 parts of benzoyl peroxide are absorbed onto another 100 parts of the screened product and the results also mixed into a paste (II) with
  7 parts bis-GMA
  8 parts triethyleneglycol dimethacrylate.

A liquid (III) was prepared from
  13 parts phosphoric acid
  15 parts hydroxyethyl methacrylate
  60 parts water
  12 parts polymethacrylated polysulfonate (Prep. 5).

1 part each of Pastes I and II and of Liquid II were mixed and applied between etched tooth enamel and a metal plate of Resilloy (Renfert, Germany, mfr.). Light pressure was exerted of the plate. The adhesive mixture solidified in 2 minutes.

5 minutes later the cemented sample was pulled apart with a tensile-strength testing apparatus at a load of 5.6 N/mm².

EXAMPLE 12. AN EXPANDING LIGHT-CURING CAVITY LINER

A light-curing composite cement is prepared from
  50 parts bis-GMA
  50 parts triethyleneglycol dimethacrylate
  1 part camphor quinone
  1 part butyl dimethylaniline
  10 parts polymethacrylated polymaleic acid (Prep. 3)
  40 parts microfine silanized silicic acid
  240 parts Ceramfil Beta, Aqua Set ionomer-cement powder.

The composite cement completely cures to a layer thickness of 3 mm in 20 seconds of irradiation with the halogen lamp. The polymerization shrinkage in water is measured at 0.0% and, 30 minutes later the sample exhibits expansion of 0.24% and, in 16 hours, of 0.80%. The value hardly varies subsequently. Given these properties, this composite cement is preferable as a cavity liner below a tooth-filling material. Much of the polymerization shrinkage of the material can be compensated by its expansion properties.

EXAMPLE 13.

A polymerizable plaster was prepared by covering 90 parts of Moldano plaster (Bayer) with an alcoholic solution of 10 parts of the Resin 1 from Example 1 and withdrawing the solvent.

The resulting plaster powder was mixed into a fluid pulp with a mixture of 25 parts of water, to which had been added 1% N,N-bis-hydroxyethyl para-toluidine and 3% sodium benzene sulfonate, and 75 parts of hydroxyethyl methacrylate.

The mixture was poured into a mold. It cured in approximately 2 minutes.

The mold was removed, leaving an excellent cast that was hardly brittle at all and exhibited high resistance to scratching.

EXAMPLE 14. CONTROL

The procedure described with reference to Example 13 was followed, mixing, however, the untreated plaster into a fluid pulp with water. The mixture took 30 minutes to set and the resulting cast was very brittle and easy to scratch.

What is claimed is:

1. A polymerizable cement mixture comprising
   (a) at least one polymerizable unsaturated monomer, oligomer or prepolymer containing an acid group or a reactive acid derivative thereof,
   (b) at least one finely divided reactive filler that can react ionically with the acids or acid derivative of (a), and
   (c) a curing agent.

2. A mixture according to claim 1, wherein (a) contains at least two polymerizable groups and at least two acid groups or reactive derivatives thereof.

3. A mixture according to claim 1, wherein (a) contains at least three polymerizable groups and at least three acid groups or their reactive derivative groups.

4. A mixture according to claim 1, wherein the polymerizable unsaturated monomer, oligomer or prepolymer of
   (a) contains acrylic, methacrylic, vinyl and/or styryl groups.

5. A mixture according to claim 1, wherein the unsaturated monomer, oligomer or prepolymer
   (a) contains acrylic and/or methacrylic groups.

6. A mixture according to claim 1, wherein the acid groups of (a) are carboxylic acid radicals, the radicals

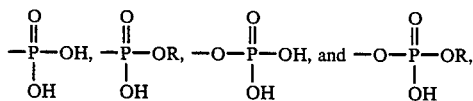

radicals —SO$_2$—H, SO$_3$H, —O—SO$_3$H, or the radicals

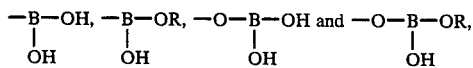

wherein R is alkyl, aryl or vinyl.

7. A mixture according to claim 1, wherein (a) comprises reactive acid derivatives selected from the group consisting of acid halides, anhydrides, or acid amides, nitriles, or esters that hydrolyze readily into the acid.

8. A mixture according to claim 1, wherein (a) comprises a halophosphoric acid ester of bis-GMA.

9. A mixture according to claim 1, wherein (a) comprises an oligomeric or prepolymeric backbone to which are bonded both polymerizable unsaturated groups and acid radicals, their salts, or their reactive derivatives.

10. A mixture according to claim 9, wherein the oligomeric or prepolymeric backbone is a homo- or copolymer of an ethylenically unsaturated monomer.

11. A mixture according to claim 10, wherein (a) comprises poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated poly- chlorophosphoric acid, poly(meth)acrylated polysulfonate or poly(meth)acrylated polyboric acid.

12. A mixture according to claim 9, wherein the oligomeric or prepolymeric backbone is a polyester, polyamide, polyether, polysulfone, polyphosphazene or polysaccharide.

13. A mixture according to claim 1, wherein (a) is a polymerizable unsaturated oligomer or polymer having a molecular weight of at least 500.

14. A mixture according to claim 1, wherein (a) is a polymerizable unsaturated prepolymer having a molecular weight of at least 1,500.

15. A mixture according to claim 1, wherein (a) is a polymerizable unsaturated prepolymer having a molecular weight of at most 100,000.

16. A mixture according to claim 1, wherein (a) is a polymerizable unsaturated prepolymer having a molecular weight of at most 20,000.

17. A mixture according to claim 1, wherein (a) contains further aldehyde, epoxide, isocyanate, or halotriazine groups in addition to the acid groups and polymerizable groups.

18. A mixture according to claim 1, additionally containing other polymerizable unsaturated monomers, oligomers and/or prepolymers that do not have acid groups or reactive acid-derivative groups that hydrolyze readily.

19. A mixture according to claim 1, additionally containing other compounds that have acid groups or their reactive acid-derivative groups that hydrolyze readily but do not have unsaturated and polymerizable groups.

20. A mixture according to claim 1, wherein the polymerizable compounds that have acid groups or acid derivative groups are present in a proportion of at least 5% of the polymerizable compounds.

21. A mixture according to claim 1, wherein the polymerizable compounds that have acid groups or acid-derivative groups are present in a portion of about 20% to 60% of the polymerizable compounds.

22. A mixture according to claim 1, wherein the reactive fillers (b) are metal compounds, glasses or ceramics or zeolites that contain metal compounds, oxidizable metals, and boron nitride, as well as the products derived from sintering mixtures of these metal compounds or of glasses or ceramics that contain them 23. A mixture according to claim 1, wherein (b) comprises a metal oxide or metal hydroxide.

24. A mixture according to claim 1, wherein (b) comprises silicate-cement powders or ion-leaching glasses.

25. A mixture according to claim 1, wherein (b) comprises finely powdered silver or silver alloys sintered with finely powdered ion-leaching glass or silicate-cement powders.

26. A mixture according to claim 1, which contains further inorganic or organic nonreactive filler.

27. A mixture according to claim 1, wherein the total filler content is between 10 and 95% of the mixture and the proportion of reactive filler (b) in the total filler content is at least 5%.

28. A mixture according to claim 1, wherein the total filler content is between 10 and 95% of the mixture and the proportions of reactive filler (b) in the total filler content is at least 30%.

29. A mixture according to claim 1, wherein the curing agent is a polymerization catalyst or system.

30. A mixture according to claim 1, wherein the curing agent is a photoinitiated polymerization catalyst comprising a mixture of an α-diketone and a tertiary amine and/or a tertiary phosphine.

31. A mixture according to claim 1, wherein (c) is a polymerization catalyst system comprising two separate constituents, one an organic peroxide and the other a tertiary amine, a sulfur compound wherein sulfur is present in oxidation state +2 or +4, or a mixture of both, or contains bivalent chelating metal ions.

32. A mixture according to claim 31, wherein the constituent of the bicomponent system that contains the sulfur compound contains no polymerizable compounds that have acid or acid groups but contains at least one polymerizable monomer with hydroxyl groups.

33. A method for repairing, filling, veneering or lining an oxidic, mineral, vitreous, ceramic, metallic or biological substrate, comprising applying to said substrate a mixture according to claim 1, and causing that mixture to harden.

34. A method for adhering (a) an oxidic, mineral, vitreous, ceramic, metallic or biological substrate to (b) an oxidic, vitreous, ceramic, metallic, biological or acrylic substrate, comprising the steps of
  (c) applying to said substrate (a) a mixture according to claim 1;
  (d) bringing said substrate (b) in good contact with said mixture on said substrate (a) and
  (e) causing that mixture to harden.

35. A method according to claim 33, wherein said biological substrate is hard dental tissue or bone.

36. A method for producing a shaped object, comprising moulding a mixture according to claim 1 into a predetermined shape, and causing that mixture to harden.

* * * * *